US00PP30801P3

(12) United States Plant Patent
van Langen

(10) Patent No.: US PP30,801 P3
(45) Date of Patent: Aug. 13, 2019

(54) ***ECHEVERIA* PLANT NAMED 'TSAECH1710'**

(50) Latin Name: ***Echeveria* hybrid**
Varietal Denomination: TSAECH1710

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/350,316

(22) Filed: Oct. 31, 2018

(65) Prior Publication Data

US 2019/0141875 P1 May 9, 2019

(30) Foreign Application Priority Data

Nov. 8, 2017 (QZ) ..... PBR 2017/2836

(51) Int. Cl.
*A01H 5/00* (2018.01)
*A01H 6/32* (2018.01)
*A01H 6/00* (2018.01)
*A01H 5/12* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
CPC ..... A01H 5/00
See application file for complete search history.

*Primary Examiner* — Annette H Para
(74) *Attorney, Agent, or Firm* — Samuel R. McCoy, Jr.

(57) ABSTRACT

A new and distinct *Echeveria* plant named 'TSAECH1710' which is characterized by improved vigor, obovate succulent foliage arranged in a basal rosette, glaucous grey foliage which is suffused pink and margined with a dark, vibrant pink at and towards the apex, as well as the stability of these characteristics from generation to generation.

3 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'TSAECH1710'.

CROSS REFERENCE TO RELATED APPLICATIONS

This application claims priority to the Community Plant Variety Rights application number 2017/2836, filed Nov. 8, 2017, which is herein incorporated by reference.

BACKGROUND OF THE INVENTION

Parentage: 'TSAECH1710' is a hybrid seedling selection resulting from the controlled pollination of an unnamed *Echeveria pulidonis* x *Echeveria* 'Perle von Numberg' hybrid plant (not patented), the seed parent, with an unnamed *Echeveria lilacina* plant (not patented), the pollen parent. The crossing was made by the inventor in the winter of 2013 at a commercial greenhouse in Heerhugowaard, the Netherlands. In the autumn of 2014, one seedling was observed which exhibited unique growth and foliage characteristics. The seedling was isolated for further evaluation in order to confirm the distinctness and stability of the characteristics first observed. Upon confirmation of distinctness and stability, 'TSAECH1710' was selected for commercialization in the winter of 2014.

Asexual Reproduction: Asexual reproduction of the new cultivar 'TSAECH1710', by way of rooting leaf cuttings, was first initiated in the summer of 2015 at the inventor's commercial greenhouse in Heerhugowaard, the Netherlands.

Through five subsequent generations, the unique features of this cultivar have proven to be stable and true to type.

SUMMARY OF THE INVENTION

The cultivar 'TSAECH1710' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1710'. These characteristics in combination distinguish 'TSAECH1710' as a new and distinct *Echeveria* cultivar:

1. 'TSAECH1710' exhibits improved plant vigor and a fast rate of growth; and
2. 'TSAECH1710' exhibits obovate succulent foliage which is curved upwards and arranged in a basal rosette; and
3. 'TSAECH1710' exhibits foliage which is upright at the center of the rosette, becoming progressively more relaxed towards the outer whorls of the rosette; and
4. 'TSAECH1710' exhibits glaucous grey foliage which is suffused pink and margined with a dark, vibrant pink at and towards the apex.

BOTANICAL DESCRIPTION OF THE PLANT

Figure 1:
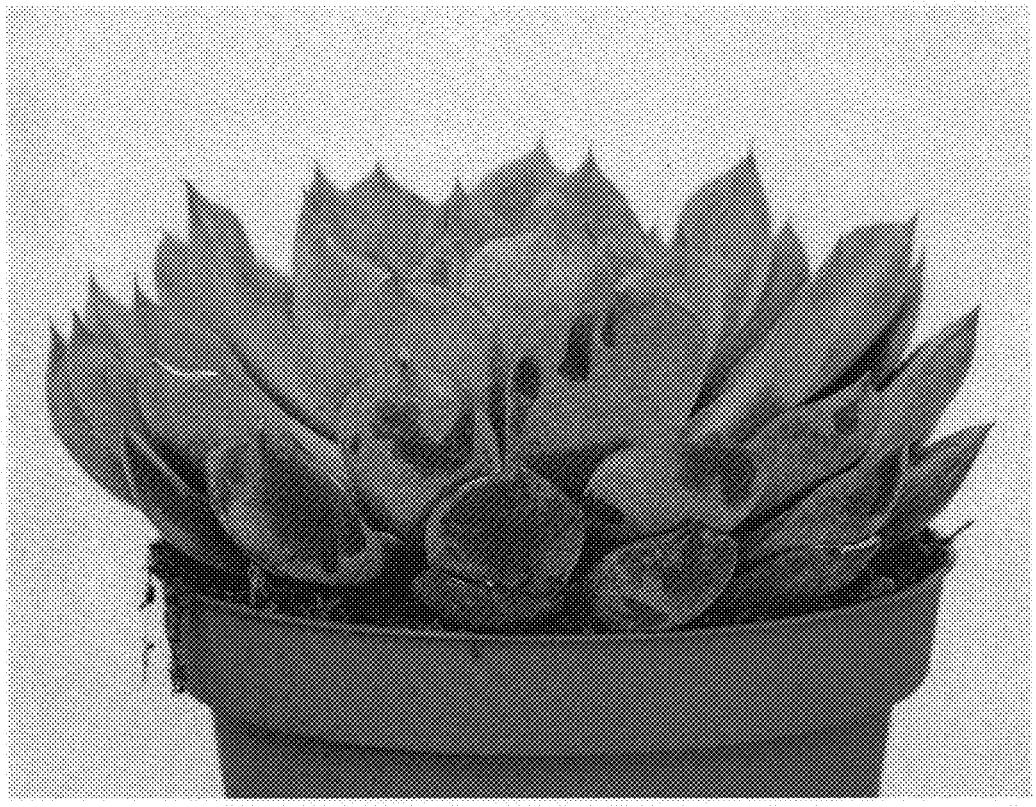
FIG. 1 illustrates, as nearly true as it is reasonably possible to make the same in color photographs of this type, an exemplary plant of 'TSAECH1710' grown in a commercial greenhouse in Heerhugowaard, the Netherlands. This plant is approximately 9 months old, shown planted in a 9 cm container.
Figure 2:
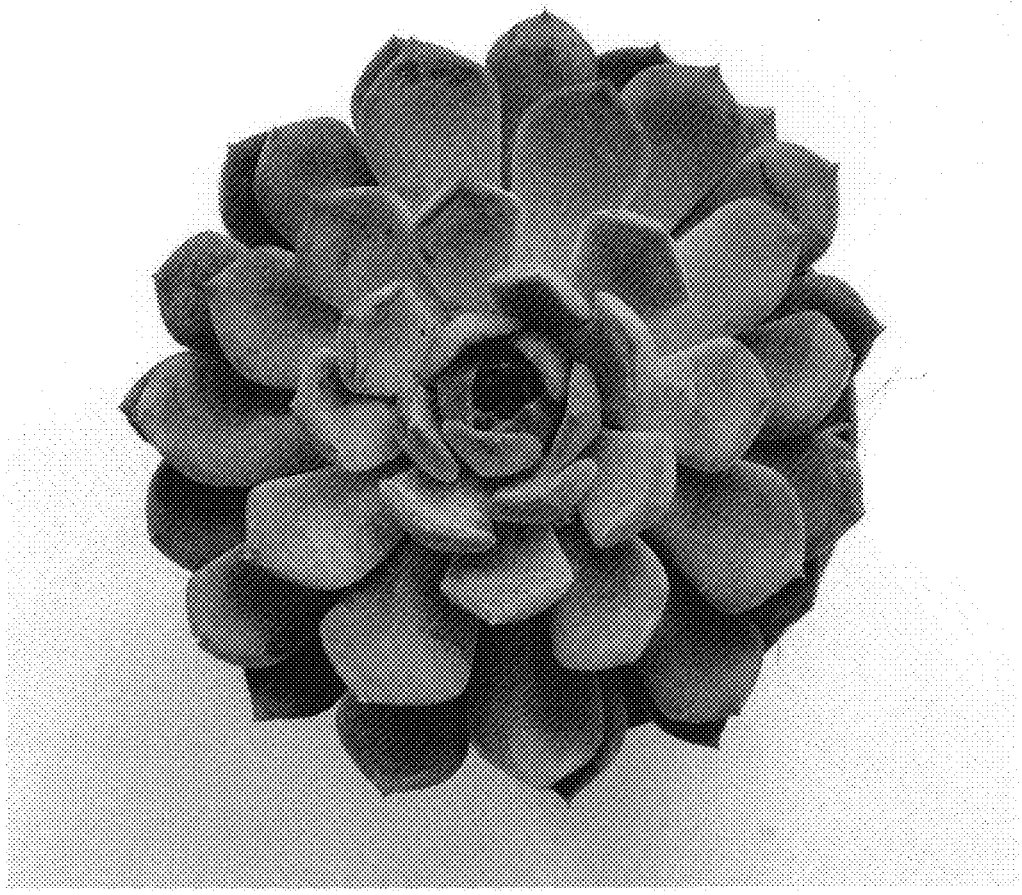
FIG. 2 illustrates, as nearly true as it is reasonably possible to make the same in color photographs of this type, the typical foliage arrangement of 'TSAECH1710'.
Figure 3:
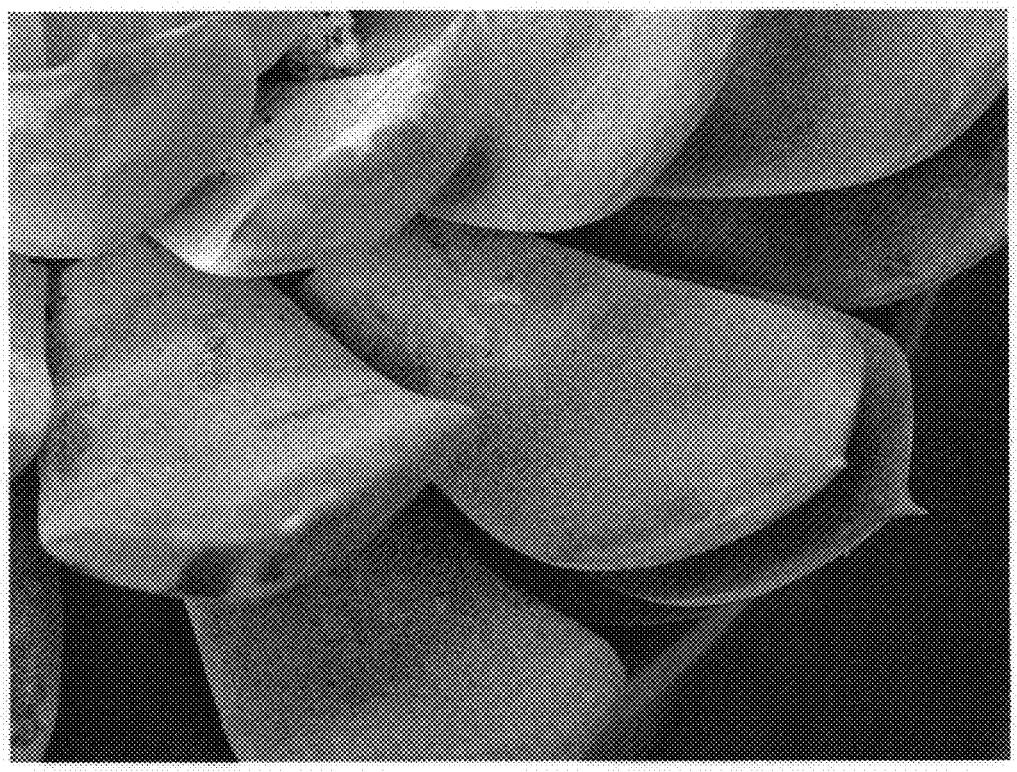
FIG. 3 illustrates, as nearly true as it is reasonably possible to make the same in color photographs of this type, the typical mature foliage of 'TSAECH1710'.

The following observations and measurements made in August of 2018 describe averages from a sample set of six specimens of 9 month old 'TSAECH1710' plants grown in 10.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1710' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1710' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—6.0 cm.

*Plant spread*.—Average of 13.0 cm.

*Growth rate*.—Moderate.

*Plant vigor*.—Moderate.

*Propagation*.—Type — Leaf cuttings. Time to initiate rooting — Approximately 21 days at 18 degrees Celsius. Crop time — Approximately 35 weeks to produce a marketable plant in an 11 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 54 leaves per rosette.

*Shape*.—Obovate.

*Dimensions*.—5.6 cm long, 2.3 cm wide, and 0.7 cm thick, on average.

*Aspect*.—Very slightly concave and slightly to moderately curved upward.

*Attitude*.—Younger foliage near the center of the rosette is very upright; foliage becoming progressively more relaxed towards the outer whorl of the rosette.

*Apex*.—Apiculate.

*Base*.—Cuneate.

*Margin*.—Entire; not undulated or lobed.

*Pubescence, texture and luster of the adaxial surface*.—Glabrous, smooth, and matte; moderately glaucous.

*Pubescence, texture and luster of the abaxial surface*.—Glabrous, smooth, and matte; moderately glaucous.

*Color*.—Juvenile foliage, adaxial surface — Yellow-green, nearest to RHS 148B, and fading lighter towards the base, nearest to RHS 147D; suffused with greyed-green towards the apex, nearest to RHS 197A; narrowly margined greyed-red at and near the apex, nearest to RHS 181B; the epicuticular glaucous wax covering the leaf surface is greyed-green, nearest to N189C. Juvenile foliage, abaxial surface — Yellow-green, nearest to RHS 148C, and becoming a light shade of greyed-green towards the base, nearest to RHS 194C; suffused with a darker shade of greyed-green towards the apex, nearest to RHS 197A; narrowly margined greyed-red at and near the apex, nearest to RHS 181A; the epicuticular glaucous wax covering the leaf surface is greyed-green, nearest to N189C. Mature foliage, adaxial surface — Nearest to in between yellow-green, RHS 148A, and greyed-green, RHS 197A, and fading lighter towards the base, nearest to RHS 195B; narrowly margined greyed-red at and near the apex, nearest to RHS 181A; the epicuticular glaucous wax covering the leaf surface is greyed-green, nearest to N189C. Mature foliage, abaxial surface — Greyed-green, nearest to RHS 197A, and lightly suffused with yellow-green, nearest to RHS 148A; fading lighter towards the base, nearest to RHS 195B; narrowly margined greyed-red at and near the apex, nearest to RHS 181A; the epicuticular glaucous wax covering the leaf surface is greyed-green, nearest to N189C.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

The seed parent, an unnamed *Echeveria* hybrid plant (not patented), is no longer in cultivation or otherwise available therefore a comparison is not possible.

Plants of the new cultivar 'TSAECH1710' differ from the pollen parent, an unnamed *Echeveria lilacina* plant (not patented), in the following characteristics described in Table 1 below.

TABLE 1

| Characteristic | 'TSAECH1710' | Pollen parent |
|---|---|---|
| Rate of growth. | Faster than the pollen parent. | Slower than 'TSAECH1710'. |
| Leaf width. | Narrower than the pollen parent. | Wider than 'TSAECH1710'. |
| General coloration of the mature foliage. | Greyed-green, lightly suffused pink, and margined with a vibrant pink at and near the apex. | Very light grey, nearly white, and suffused pink. |

COMPARISONS WITH THE CLOSEST KNOWN COMPARATOR

Plants of the new cultivar 'TSAECH1710' differ from the closest known commercial comparator, the common form of the species *Echeveria pelusida* (unnamed and not patented), in the following characteristics described in Table 2 below.

TABLE 2

| Characteristic | 'TSAECH1710' | *Echeveria pelusida* |
|---|---|---|
| Plant vigor. | More vigorous than *Echeveria pelusida* with less occurrence of leaf necrosis. | Less vigorous than 'TSAECH1710' with a greater occurrence of foliage necrosis. |
| General coloration of the foliage. | Greyed-green, lightly suffused pink, and margined with a vibrant pink at and near the apex. | Greyed-green with a red margin. |

That which is claimed is:

1. A new and distinct variety of *Echeveria* hybrid plant named 'TSAECH1710', substantially as described and illustrated herein.

* * * * *